US012799454B2

(12) United States Patent
Yang et al.

(10) Patent No.: US 12,799,454 B2
(45) Date of Patent: Nov. 17, 2026

(54) FETAL CELL CAPTURE MODULE AND MICROFLUIDIC CHIP FOR FETAL CELL CAPTURE AND METHODS FOR USING THE SAME

(71) Applicant: WISDOM HEALTHY BIOTECH (XIAMEN) COMPANY LIMITED, Xiamen (CN)

(72) Inventors: Chaoyong Yang, Xiamen (CN); Huimin Zhang, Xiamen (CN); Yuanyuan Yang, Xiamen (CN); Yilong Liu, Xiamen (CN); Zhi Zhu, Xiamen (CN)

(73) Assignee: WISDOM HEALTHY BIOTECH (XIAMEN) COMPANY LIMITED, Xiamen (CN)

( * ) Notice: Subject to any disclaimer, the term of this patent is extended or adjusted under 35 U.S.C. 154(b) by 1055 days.

(21) Appl. No.: 17/802,760

(22) PCT Filed: Feb. 24, 2021

(86) PCT No.: PCT/CN2021/077731
§ 371 (c)(1),
(2) Date: Aug. 26, 2022

(87) PCT Pub. No.: WO2021/170009
PCT Pub. Date: Sep. 2, 2021

(65) Prior Publication Data

US 2023/0092810 A1 Mar. 23, 2023

(30) Foreign Application Priority Data

Feb. 26, 2020 (CN) ........................ 202010121341.X

(51) Int. Cl.
*C12N 5/078* (2010.01)
*B01L 3/00* (2006.01)

(52) U.S. Cl.
CPC ...... *C12N 5/0634* (2013.01); *B01L 3/502761* (2013.01); *C12N 5/0641* (2013.01); *B01L 2200/0652* (2013.01); *B01L 2300/0654* (2013.01); *B01L 2300/0819* (2013.01); *C12N 2509/00* (2013.01)

(58) Field of Classification Search
CPC ................ C12N 5/0641; C12N 5/0634; C12N 2509/00; C12N 5/0605; B01L 3/502761; B01L 2200/0652; B01L 2300/0654; B01L 2300/0819; B01L 3/502753; C12M 23/16; B01D 15/08; B01D 15/26; B01D 15/38; B01D 15/3804; B01D 15/3809; B01D 15/3828; B01D 63/005
See application file for complete search history.

(56) References Cited

FOREIGN PATENT DOCUMENTS

| | | |
|---|---|---|
| CN | 104364389 A | 2/2015 |
| CN | 204939452 U | 1/2016 |
| CN | 108535228 A | 9/2018 |
| CN | 111440696 A | 7/2020 |

OTHER PUBLICATIONS

Dong, J et al. Covalent chemistry on nanostructured substrates enables noninvasive quantification of gene rearrangements in circulating tumor cells. Science Advances. 2019. 5: eaav9186. 12 pages. Published Jul. 31, 2019. (Year: 2019).*
Sun, N et al. Purification of HCC-specific extracellular vesicles on nanosubstrates for early HCC detection by digital scoring. Nature Communications. 2020. 11: 4489. 12 pages. Published Sep. 7, 2020. (Year: 2020).*
Zhang, H et al. Stimuli-responsive microfluidic interface enables highly efficient capture and release of circulating fetal cells for non-invasive prenatal testing. Analytical Chemistry. 2020. 92: 9281-9286. Published May 26, 2020. (Year: 2020).*
Cui, Y et al. Mesoporous silica nanoparticles capped with disulfide-linked PEG gatekeepers for glutathione-mediated controlled release. ACS Applied Materials & Interfaces. 2012. 4: 3177-3183. (Year: 2012).*
International Search Report issued in International Application No. PCT/CN2021/077731, mailed May 31, 2021; 6 pgs.
Written Opinion issued in International Application No. PCT/CN2021/077731, mailed May 31, 2021; 7 pgs.
Search Report issued in Chinese Application No. 202010121341.X; mailed Apr. 29, 2021; 2 pgs.
First Office Action issued in Chinese Application No. 202010121341.X; mailed May 10, 2021; 16 pgs.
Dong, Jiantong, et al.; Covalent chemistry on nanostructured substrates enables noninvasive quantification of gene rearrangements in circulating tumor cells; Science Advances; vol. 5, eaav9186; Jul. 31, 2019; pp. 1-12.

(Continued)

*Primary Examiner* — David W Berke-Schlessel
*Assistant Examiner* — Susan E. Fernandez
(74) *Attorney, Agent, or Firm* — HAUPTMAN HAM, LLP

(57) ABSTRACT

The present invention relates to a fetal cell capture module, a microfluidic chip for fetal cell capture, and methods for using the same. The fetal cell capture module comprises a cell capture carrier and recognition molecule(s) for specific capture the cell(s). The recognition molecule is attached to the surface of the carrier via an organic conjugate L comprising disulfide bonds. The surface of the chip is modified with recognition molecules that specifically capture fetal cells via organic conjugates comprising disulfide bonds. The recognition molecule, after capturing the cell, achieves the release of the cell by chemically cleaving the disulfide bonds in the organic coupling conjugate. The present invention enables the capture of fetal cell(s) from whole blood without pre-treatment with a high capture rate, low cell loss, simple and accurate cell release operation, and the efficient and noninvasive release of fetal cells and whole genome analysis.

16 Claims, 4 Drawing Sheets

(56) References Cited

OTHER PUBLICATIONS

Supplementary search report issued in Chinese Application No. 202010121341.X; mailed Dec. 29, 2021; 1 pgs.
Second Office Action issued in Chinese Application No. 202010121341.X; mailed Jan. 14, 2022; 19 pgs.

* cited by examiner

Schematic diagram of microfluidic chip
Figure 1A
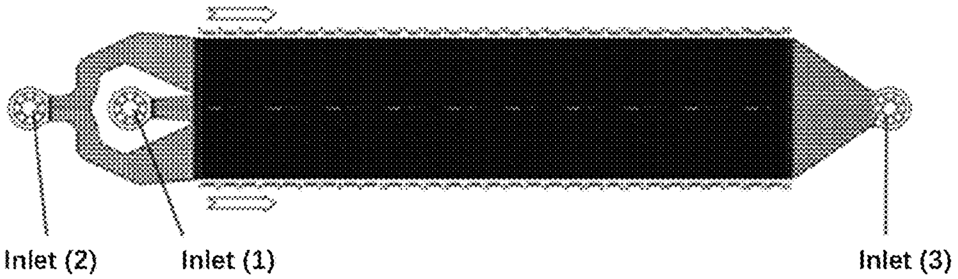
Photograph of microfluidic chip (pigment was injected to fill the channel)
Figure 1B
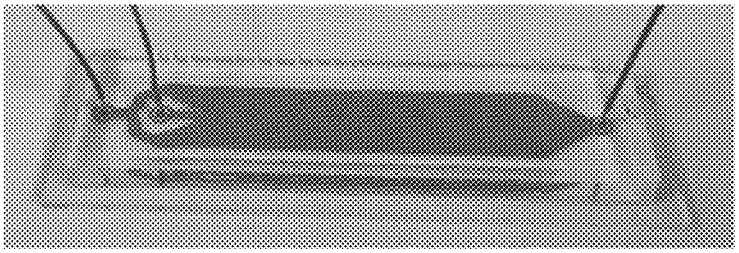
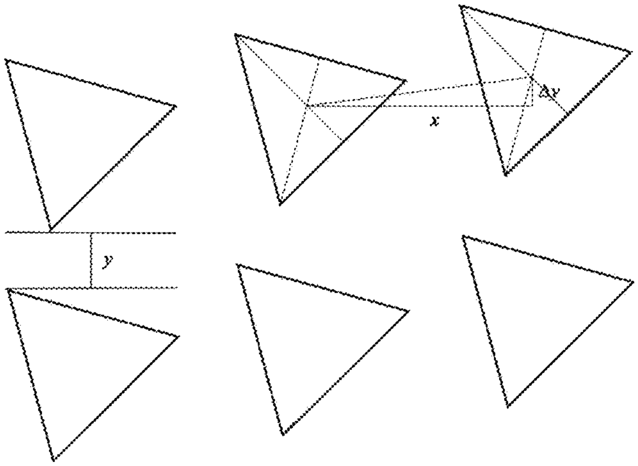
Figure 2

FETAL CELL CAPTURE MODULE AND MICROFLUIDIC CHIP FOR FETAL CELL CAPTURE AND METHODS FOR USING THE SAME

RELATED APPLICATIONS

The present application is a U.S. National Phase of International Application Number PCT/CN2021/077731, filed Feb. 24, 2021, and claims priority to Chinese Application Number 202010121341.X, filed Feb. 26, 2020.

TECHNICAL FIELD

The present application relates to the field of cell capture. Specifically, it relates to fetal cell capture module and microfluidic chip for fetal cell capture and methods for using the same

TECHNICAL BACKGROUND

Improving reproductive health and preventing and controlling major birth defects is one of the important goals of a healthy China. After the implementation of the "comprehensive two-child" policy, the number of senior pregnant women has increased, and birth defects prevention and control are facing more challenges. "Prenatal screening and diagnosis" is the most important means of preventing birth defects. Amniocentesis, chorionic villus biopsy, and cord blood aspiration, the current gold standard for prenatal diagnosis, have limitations such as being invasive, difficult to sample, and having a narrow time window for sampling, which can easily lead to complications and miscarriage. The sensitivity and accuracy of noninvasive prenatal testing methods such as serological screening and ultrasonography are poor, making it difficult to replace invasive screening methods. Therefore, the establishment of a safe and accurate prenatal diagnosis system is an important issue to reduce the birth of defective children and improve the quality of the population. The development of new non-invasive prenatal testing techniques has important clinical significance and is one of the main directions of current development in the field of prenatal diagnosis.

The core of non-invasive prenatal testing technology is to analyze the trace fetal genetic information present in the peripheral blood of pregnant women to achieve genetic screening and diagnosis. There are two sources of fetal genes in the peripheral blood of pregnant women: 1) free DNA fragments derived from apoptotic fetal cells. Non-invasive Prenatal Testing (NIPT), which has been studied for this purpose, has opened a new chapter in prenatal testing and effectively complemented the existing prenatal screening system, resulting in an increased detection rate of trisomy to 99%. However, free DNA has the following characteristics: a) it is mainly derived from the apoptosis of placental cells and has a high degree of DNA sequence fragmentation, generally considered to be around 166 bp on average; b) there is a large amount of maternal DNA background interference; c) the accuracy of genetic testing depends on the amount of fetal DNA. Therefore, although free DNA-based NIPT technique can improve the detection rate of autosomal aneuploidy (trisomy 21, 18, 13), it is difficult to detect fetal chromosomal disorders such as sex chromosome abnormalities, chromosomal balancing structures (translocations and inversions), and large segmental deletions. False-negative/positive results can be caused by the presence of restrictive placental chimerism or maternal chromosomal abnormalities. NIPT can only be used as an autosomal aneuploidy screening technique to improve the detection rate of Down's syndrome, but cannot be extended to other genetic disorders, and still requires invasive gold standard karyotyping for clinical confirmation. 2) Circulating Fetal Cells (CFCs) are fetal nucleated cells present in maternal peripheral blood, derived from the shedding of trophoblast cells or from fetal cells that enter the maternal circulation during the exchange of maternal blood substances. Circulating fetal cells carry complete cell biological information and are considered to be the most promising candidates for non-invasive prenatal diagnosis. The main types of circulating fetal cells include trophoblasts, leukocytes, and nucleated red blood cells etc. Among them, trophoblasts and nucleated red blood cells are the most suitable targets for prenatal diagnosis because they contain specific surface antigens, exist only during gestation, and have no interference between fetus and fetus.

However, the main reason why circulating fetal cells have not been used for clinical application so far is that the technical barriers to fetal cell capture/enrichment in peripheral blood are too high. The main technical difficulties include: 1) Extremely low levels of CFCs (1-10/mL) and extremely high maternal blood cell background (erythrocytes: 109/mL, leukocytes: 107/mL). 2) low differentiation of CFCs from blood cell size (CFCs: 9~13 μm; leukocytes: 7~15 μm; erythrocytes: 6~8 μm), leading to difficulty in the physical separation and dependent on markers for separation. (3) Low efficiency of CFCs release with complicated operation. The majority of current methods are used to obtain high-purity fetal cells by immunostaining followed by the application of single-cell micro-manipulator and laser microdissection (LCM), which are complicated and inefficient. The use of LCM to release captured cells often increases the complexity, cost and flexibility of the application and has a high technical threshold. In contrast, physical separation methods, although not marker-dependent, are prone to cell loss and thus do not enrich fetal cells efficiently. In addition, these methods require initial enrichment such as erythrocyte lysis, density centrifugation or dilution, which often leads to loss or damage of fetal cells. Therefore, there is still a great need to develop technologies that can capture CFCs in a high-throughput, high-purity manner and enable nondestructive and rapid cell release.

SUMMARY OF THE INVENTION

To solve the problems of low capture efficiency, low purity, high cost and difficulty in whole genome analysis by existing fetal cell analysis techniques, the following fetal cell capture module, microfluidic chip for fetal cell capture and methods for using the same are proposed to achieve efficient and high purity capture and release of fetal cells and to enable fetal whole genome analysis.

On the one hand, the invention provides a fetal cell capture module comprising a cell capture carrier and one or more recognition molecules for specific capture of the cell(s), the recognition molecule being attached to the surface of the cell capture carrier via an organic conjugate L comprising one or more disulfide bonds. After capturing the cell(s) by the recognition molecules, the cell(s) are released by chemically cleaving the disulfide bonds in the organic conjugate L. One or more of dithiothreitol (DTT), tris(2-carboxyethyl)phosphine (TCEP) or glutathione (GSH), preferably dithiothreitol, may be used as the chemical cleavage reagent.

In some embodiments, the recognition molecule includes but are not limited to, nucleic acid aptamer, protein receptor, polypeptide, antibody, and organic small molecule compound, etc. In some embodiments, the recognition molecule is antibodies, in particular, one or both of an epithelial adhesion factor antibody (anti-EpCAM antibody) and an anti-transferrin receptor antibody (anti-CD71 antibody); or the recognition molecule is other fetal cell-specific recognition antibody, in particular, other trophoblasts cell-specific recognition antibody.

In some embodiments, the fetal cell is nucleated red blood cell or trophoblast cell, preferably trophoblast cell. In some embodiments, the fetal cell, in particular trophoblast cell, is obtained from peripheral blood and/or cervical swab dispersion.

In some embodiments, the organic conjugate L has the formula:

-A-X—,

A is a group with a sulfur bond at one end and covalently attached to the capture carrier at the other end; depending on the material of the capture carrier, different A groups may be chosen to be attached to the capture carrier, as is known to those skilled in the art;

X is a group with a sulfur bond at one end and directly or indirectly attached to the recognition molecule at the other end;

X has the formula:

—S—$(B)_p$-D-, p=0-10,

S is sulfur,

D is a group for attachment to the recognition molecule; the choice of the group for attachment of the organic conjugate to the recognition molecule is well known in the art. Usually, D can be chosen from amide group, aminoacyl, thioxo, succinimidyl, alkynyl, azide group, etc.

B is

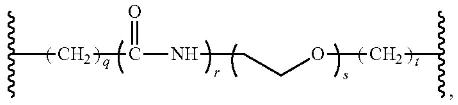

wherein, q, r, and t is 0-10, preferably 1-5, respectively; s is 0-115, preferably 20-50; and B can be connected to S by either end and to D by the other end.

In some embodiments, the organic conjugate L has the formula:

-A-X—, wherein,

One end of A is a monosulfur bond for linking with X, and the other end is fixed to the capture carrier. The non-S structural moiety of A can be selected based on different capture carrier materials, so that A is covalently linked to the capture carrier. In some embodiments of the invention, A includes, but is not limited to

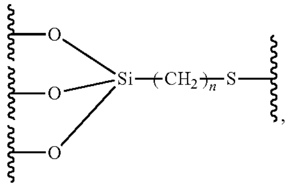

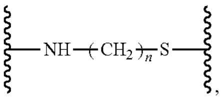

-continued

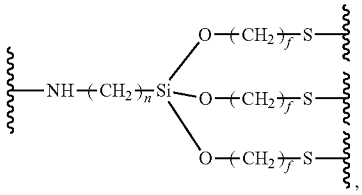

, or

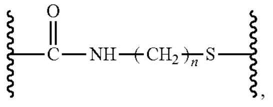

wherein A is covalently linked to the capture carrier via the non-sulfur bond end, wherein n=1-10, f=1-10; preferably, n=3-8 and f=2-8.

One end of X is a monosulfur bond for linking with A, constituting a disulfide bond in the organic conjugate L; the other end of X is directly or indirectly linked with the recognition molecule, for example, by a bond in a group such as amide, succinimide, etc. The non-S structural moiety of X may contain, in addition to the group used to link with the recognition molecule, other connecting moieties, such as molecular moieties of polyethylene glycol derivatives, which can be straight or branched chain structures. The molecular weight distribution of the polyethylene glycol is preferably 200-5000, for example, 200, 500, 600, 800, 1000, 1500, 2000, 3000, 5000, more preferably 1000-2000.

In some embodiments, X comprises, but is not limited to,

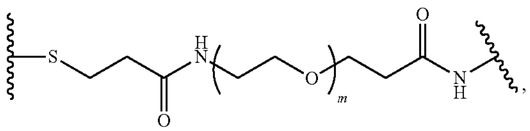

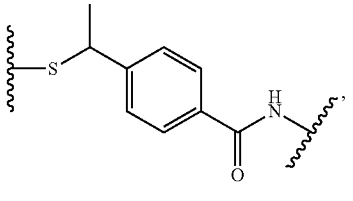

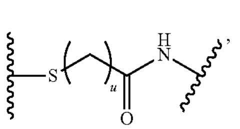

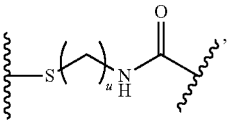

and preferably X includes but is not limited to

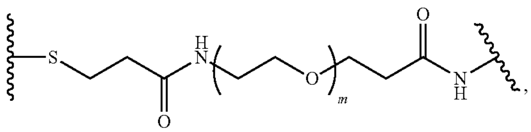

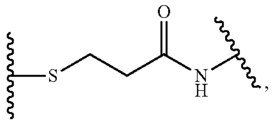

-continued

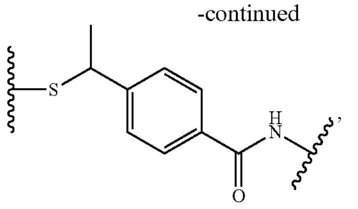

wherein the sulfur end of X is covalently attached to A to form a disulfide bond, with the other end of X being directly or indirectly connected to the recognition molecule.

m=0-115, u=1-10; preferably, m=20-50, u=2-8.

In some embodiments, the organic conjugate L may comprise other disulfide bond(s) in addition to the disulfide bond used to covalently link A to X.

In some embodiments, the organic conjugate L is selected from one or more of the following structures:

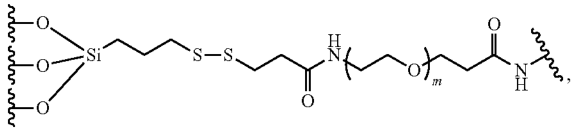

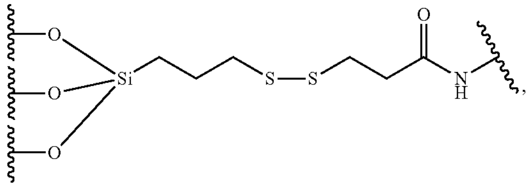

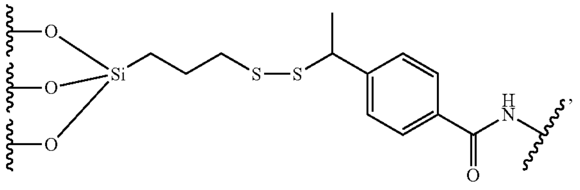

wherein, m=0-115; preferably, m=20-50.

In some embodiments, the organic conjugate L is directly linked to the recognition molecule. In some embodiments, the organic conjugate L is indirectly linked to a recognition molecule. In the preferred embodiments, the organic conjugate L is indirectly linked to a biotinylated recognition molecule after modified by streptavidin.

The cell capture carrier referred to in the invention may be all substrate, interface, or cell capture device capable of immobilizing the recognition molecule(s) for cell capture. These carriers may not be involved in cell isolation or capture, but only function to immobilize recognition molecule(s), and these carriers may also have specific isolation function that work together or in concert with the recognition molecule(s) immobilized thereon to achieve cell capture.

In some embodiments, the cell capture carrier includes magnetic bead, microfluidic chip, polystyrene microsphere, or filter membrane, such as micron-scale magnetic bead, nanoscale magnetic bead, fishbone microfluidic chip, micro-column microfluidic chip, and the like. The material of the magnetic bead can be commercialized or self-made ferro-ferric oxide spheres. The commercialized suppliers can be Thermo Fisher Co., Suzhou VDO Biotech Co., Ltd. and the like. The production method can be oil phase synthesis method, hydrothermal method and the like. The microfluidic chip can be obtained by moulding and etching method, and the specific operation process can be referred to "Microfluidic Chip Laboratory" and "Illustrated Microfluidic Chip Laboratory" of Science Press. The material of the chip can be selected from silicon substrate, polydimethylsiloxane (PDMS), polymethyl methacrylate (PMMA), polycarbonate (PC), cycloolefin polymer and the like. These cell capture carriers can be devices conventional used in the art for cell isolation, and the person skilled in the art has basic knowledge of using these devices.

The specific operation and process conditions for the obtaining or preparation of the cell capture carrier described in the invention can be carried out with reference to the manner well known in the art, for example, see "Circulating Tumor Cells: Advances in Basic Science and Clinical Applications (Chinese Translation)" published by Science Press (U.S.) Richard J. Cote, etc., and "Modern Medical Laboratory Instruments and Experimental Techniques", etc.

On the other hand, the invention provides a method of using the capture module comprising bringing the capture module in contact with a liquid comprising fetal cell(s) to enable capture of the fetal cell(s).

In some embodiments, the liquid comprises peripheral blood, cervical swab dispersion or suspension of a pregnant mammal or pregnant woman, or non-pregnant peripheral blood, buffer or culture comprising fetal cell(s). In some embodiments, the liquid is peripheral blood of a pregnant mammal, or a cervical swab dispersion or suspension. In some embodiments, the liquid is a buffer or culture comprising fetal cell(s). In some embodiments, the liquid is non-pregnant peripheral blood or cervical swab dispersion/suspension comprising fetal cell(s), wherein the fetal cell(s) is/are artificially added to the non-pregnant peripheral blood or cervical swab dispersion/suspension.

In some embodiments, the liquid is directly contacted with the capture module without pre-isolation treatment.

In some embodiments, the capture module that has captured the fetal cell(s) is contacted with a chemical cleaving agent that breaks the disulfide bond(s) to achieve the release of the fetal cell(s). In some embodiments, the chemical cleaving agent is dithiothreitol (DTT), tris(2-carboxyethyl) phosphine (TCEP), glutathione (GSH). Preferably the cleaving agent is dithiothreitol.

On the other hand, the invention provides a microfluidic chip for fetal cell capture, the surface of which is modified via organic conjugate(s) L comprising one or more disulfide bonds by one or more recognition molecules that specifically capture the fetal cell(s). The recognition molecule, after capturing the cell, achieve the release of the cell by chemically cleaving the one or more disulfide bonds in the organic conjugate L.

When a liquid containing cell(s) is introduced into the chip, the cell is/are contacted with the recognition molecule(s) fixed on the surface of the chip to achieve cell capture. In some embodiments, the microfluidic chip is provided with one or more inlets, outlets, and fluidic channels for liquid passage, such as fluidic microchannel. The one or more recognition molecules are modified on the surface of the fluidic channel. In some embodiments, the fluidic microchannel, such as the inner wall of the microchannel, is further provided with a microarray comprising a plurality of microcolumns arranged in one or more rows. The spacing of adjacent microcolumns is greater than the diameter of the fetal cell to be captured, to be sufficient to allow passage of the fetal cell, in particular trophoblast cell. The one or more specific recognition molecules may be further immobilized to the surface of the microcolumns. Due to the different cell sizes, fetal cell collides with the microcolumns to achieve multiple contacts, allowing them to be effectively captured and isolated from other cells.

In some embodiments, the cross-sectional shape of the microcolumns is circular or triangular, preferably triangular, such as an equilateral triangle.

In some embodiments, the triangle has a side length of 10 to 200 μm, such as 20 μm, 30 μm, m, 50 μm, 60 μm, 70 μm, 80 μm, 90 μm, 100 μm, 110 μm, 120 μm, 130 μm, 140 μm, 150 μm, 160 μm, 170 μm, 180 μm, 190 μm. In some embodiments, the triangle has a horizontal rotation angle of 0° to 15°, such as 1°, 2°, 3°, 4°, 5°, 6°, 7° 8°, 9° 10°, 11°, 12°, 13°, 14°, 15°. Wherein, 0 degrees is set as the angle formed when one side of the triangle is parallel to the horizontal direction of the fluid microchannel. The triangle can be rotated based on any vertex of the side, and the angle of the side with the horizontal direction after rotation is the horizontal rotation angle. Rotating the triangle by a specific angle enables the three sides of the microcolumn to exhibit gradient shear stress, increasing the contact time between the fetal cell(s) and the recognition molecule(s) and improving the capture effect and purity.

In some embodiments, the horizontal distance x between the orthocenters of adjacent microcolumns in the same row is 100-150 μm, for example, 110 μm, 120 μm, 130 μm, 140 μm; the offset distance Δy of the orthocenter of the latter microcolumn relative to the orthocenter of the previous microcolumn along the vertical direction of the fluid microchannel plane is 0-20 μm, for example, 1 μm, 3.5 μm, 6.5 μm, 7.5 μm; When the microcolumns are arranged in multiple rows, the vertical spacing y from the bottom of the previous microcolumn to the top of the next microcolumn in the vertical direction along the fluid microchannel plane in the same column is 0-50 μm, such as 10 μm, 20 μm, 30 μm, 40 μm.

The microfluidic chip of the invention is provided with one or more inlets and outlets, respectively. In the preferred embodiment, the chip is provided with two inlets and one outlet for the liquid, buffer or culture solution containing cell(s) to be introduced from different inlets respectively. When the buffer is introduced into the chip together with the blood, the buffer can dilute the blood and can further improve cell capture efficiency.

In some embodiments, the material of the fluidic microchannels and/or microarrays is polydimethylsiloxane (PDMS).

In some embodiments, the chemical cleavage is achieved by using one or more of dithiothreitol, tris(2-carboxyethyl) phosphine, glutathione, etc., preferably by using dithiothreitol to achieve the chemical cleavage. Upon addition of disulfide bond cleavage reagent, the disulfide bond is broken and the antibody/antibodies that has captured fetal cell(s) is/are detached from the chip, achieving specific release of fetal cell(s). The chemical cleavage of the invention minimizes the interference with maternal cells and enables targeted release.

In some embodiments, the recognition molecule is a membrane marker that specifically recognizes fetal cell. These recognition molecules include, but are not limited to, nucleic acid aptamer, protein such as receptor, polypeptide, antibody, or small molecule. In some embodiments, the recognition molecule is an antibody, in particular, an anti-EpCAM antibody. Fetal trophoblast cell(s) in peripheral blood, derived from the intraplacental villous layer, are highly expressed of the epithelial adhesion factor, EpCAM, and therefore anti-EpCAM antibody is preferred. Or the recognition molecule is an antibody specific for other kind of fetal cell, in particular trophoblast cell.

In some embodiments, the fetal cell is nucleated erythrocyte or trophoblast cell, preferably trophoblast cell. More preferably, the nucleated erythrocyte or fetal trophoblast cell is obtained from peripheral blood and/or cervical swab dispersion.

In some embodiments, the organic conjugate L has the formula:

-A-X—,

A is a group with a sulfur bond at one end and covalently attached to the capture carrier at the other end; depending on the material of the capture carrier, different A group may be chosen to be attached to the capture carrier, as is known to those skilled in the art;

X is a group with a sulfur bond at one end and attached to the recognition molecule at the other end;

X has the formula:

$—S—(B)_p$-D-, p=0-10,

S is sulfur,

D is a group for attachment to the recognition molecule; the choice of the group for attachment of the organic conjugate to the recognition molecule is well known in the art. Usually, D can be chosen from amide group, aminoacyl, thioxo, succinimidyl, alkynyl, azide group, etc.

B is

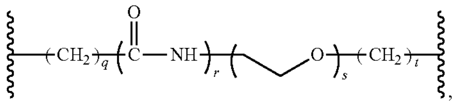

wherein, q, r, and t is 0-10, preferably 1-5, respectively; s is 0-115, preferably 20-50; and B can be connected to S by either end and to D by the other end.

In some embodiments, the organic conjugate L has the formula:

-A-X—, wherein,

One end of A is a monosulfur bond for linking with X, and the other end is fixed to the capture carrier. The non-S structural moiety of A can be selected based on different capture carrier materials, so that A is covalently linked to the capture carrier. In some embodiments of the invention, A includes, but is not limited to

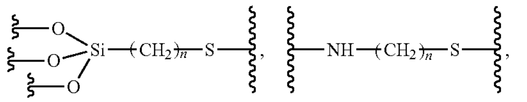

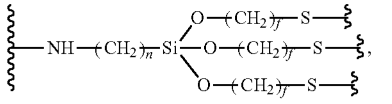

or

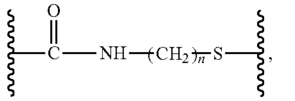

wherein A is covalently linked to the capture carrier via the non-sulfur bond end, wherein n=1-10, f=1-10; preferably, n=3-8 and f=2-8.

One end of X is a monosulfur bond for linking with A, constituting a disulfide bond in the organic conjugate L; the other end of X is directly or indirectly linked with the recognition molecule, for example, by a bond in a group such as amide, succinimide, etc. The non-S structural moiety of X may contain, in addition to the group used to link with the recognition molecule, other connecting moieties, such as molecular moieties of polyethylene glycol derivatives, which can be straight or branched chain structures. The molecular weight distribution of the polyethylene glycol is preferably 200-5000, for example, 200, 500, 600, 800, 1000, 1500, 2000, 3000, 5000, more preferably 1000-2000. In some embodiments, X includes, but is not limited to, -continued

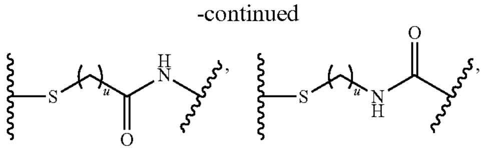

preferably selected from

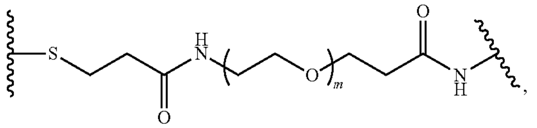

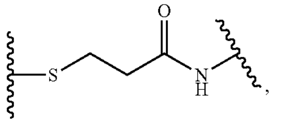

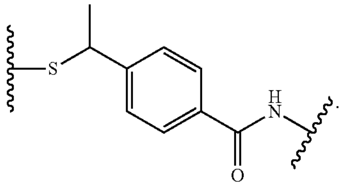

wherein the sulfur bond end of X is covalently attached to A to form a disulfide bond, with the other end being directly or indirectly connected to the recognition molecule, m=0-115, u=1-10; preferably, m=20-50, u=2-8.

In some embodiments, the organic conjugate L is selected from one or more of the following structures:

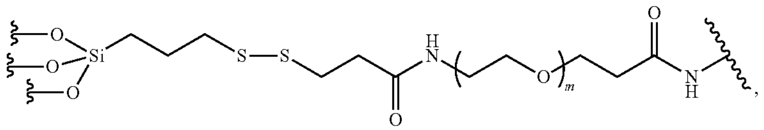

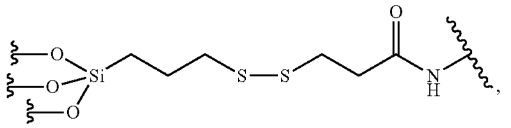

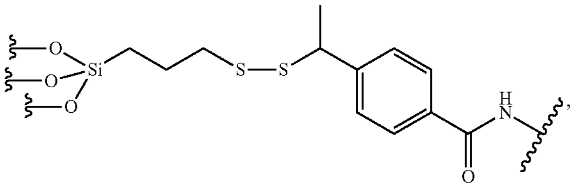

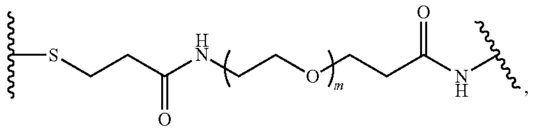

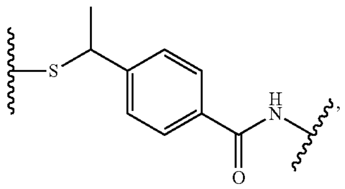

wherein, m=0-115; preferably, m=20-50.

In some embodiments, the organic conjugate L may comprise other disulfide bond(s) in addition to the disulfide bond used to covalently link A to X.

In some embodiments, the organic conjugate L is directly linked to the recognition molecule. In some embodiments, the organic conjugate L is indirectly linked to the recognition molecule. In the preferred embodiments, the organic conjugate L is indirectly linked to a biotinylated recognition molecule after modified by streptavidin.

The microfluidic chip of the invention for fetal cell capture can be prepared by methods known in the art. In some embodiments, the microfluidic chip may also be bonded to a slide for use. In some embodiments, the carrier material is glass and the bonding method is plasma bonding. The chip inlet and outlet can be made by punching a hole with a pen commonly used in the art, the size of which can be selected according to the pre-captured cells. The preferred size of the punch pen is (ID*OD, mm) 3.3×4.0, 3.3×3.5, 2.4×3.0, 2.3×2.8, 1.9×2.4, 1.6×2.1, 1.2×1.8, 0.9×1.3, 0.6×0.9, 0.5×0.8, 0.4×0.7. For example, the size of the inlet hole can be 0.4×0.7 mm, and the size of the outlet hole can be 1.2×1.8 mm.

On the other hand, the invention provides a method of using the above-mentioned microfluidic chip, comprising:

(1) obtaining a liquid containing fetal cell(s);

(2) injecting the liquid obtained in step (1) into the microfluidic chip, so that the fetal cell(s) in the liquid being brought into contact with the one or more specific recognition molecules to realize the capture of the fetal cell(s).

In some embodiments, 2-10 mL of the liquid containing the fetal cell(s) may be injected into the chip in step (1).

In some embodiments, the method further comprises the step as follows:

(3) introducing a chemical cleavage agent to the microfluidic chip to break the one or more disulfide bonds in the organic conjugate(s) and release the captured fetal cell(s).

In some embodiments, the liquid comprises peripheral blood, cervical swab dispersion or suspension of a pregnant mammal or pregnant woman, or non-maternal peripheral blood, buffer or culture solution containing fetal cell(s). In some embodiments, the liquid is peripheral blood or cervical swab dispersion or suspension of a pregnant mammal. In some embodiments, the liquid is peripheral blood, or a cervical swab dispersion or suspension of a pregnant woman. In some embodiments, the liquid is a buffer or culture solution comprising fetal cell(s). In some embodiments, the liquid is non-maternal peripheral blood or cervical swab dispersion/suspension comprising fetal cell(s), wherein the fetal cell(s) is/are artificially added to the non-maternal peripheral blood or cervical swab dispersion/suspension.

In some embodiments, the liquid is introduced directly into the microfluidic chip without pre-isolation treatment.

In some embodiments, the flow rate of the liquid passing through the microfluidic chip is 0.1-10 mL/h, preferably 0.1-1 mL/h, such as 0.1 mL/h, 0.3 mL/h, 0.5 mL/h, 1 mL/h etc., more preferably 0.5 mL/h. When the flow rate is too high, it will result in lower cell capture efficiency; too slow will result in lower capture efficiency. Therefore, for samples with a small number of cells, in order to achieve the best capture effect, an appropriate injection flow rate should be selected.

In some embodiments, after the cell(s) is/are captured in step (2), the chip can be washed with a buffer to remove biological substances such as other non-specifically bonded cells that are unrelated to the cell(s) to be captured, and then the cell(s) in step (3) are released.

In some embodiments, single base mutation analysis is performed on the released fetal cell(s). The released cell(s) is/are collected, and the genome is released by thermal lysis (e.g., at 95° C.), and digital PCR technology is used to analyze single-base mutations.

In some embodiments, the released fetal cell(s) is/are analyzed for specific expression of RNA.

In some embodiments, the released fetal cell(s) is/are subjected to whole-genome analysis after amplification. Whole-genome amplification of fetal cell(s) is performed using amplification methods routine in the field, preferably multiple displacement amplification (MDA) (commercial kit for reference is Qiagen (Germany)), Multiple Annealing and Looping Based Amplification Cycles (MALBAC) (commercial kit for reference is provided by Shanghai Yikon Medical Laboratory Co., Ltd.), etc. After cell amplification, the product is purified using column purification (for reference, the DNA purification products of Qiagen (Germany)) or magnetic beads (for reference, the magnetic bead purification kits of Beckman, Vazyme, etc.). After purification, genetic analysis is performed using sequencing technologies such as NovaSeq technology (Illumina).

In the present invention, the recognition molecule for specifically capturing the cell refers to a substance that binds to the biomolecule to be captured (or called a target molecule, such as a cell) in a specific manner through weak intermolecular interaction or covalent interaction. These recognition molecules may include: nucleic acid such as DNA, RNA, PNA; protein such as receptor, antibody; polypeptide; small organic molecule and the like. The antibody may preferably be one or more of anti-EpCAM antibody, anti-CD71 antibody, and SLY3C nucleic acid aptamer (refer to Patent ZL201310328256.0).

The protein may be modified or engineered, which means that one or more amino acids contained in the protein are changed due to the addition of new chemical groups and/or the removal of the original chemical groups. These changes can be natural or artificial. Synthetic modifications include, but are not limited to, adding chemical or biological small molecules, or reacting chemical or biological small molecules with existing groups on proteins and linking them.

The recognition molecules of the invention can be purchased commercially. For example, the sources of commercial anti-EpCAM antibody include, but are not limited to, brands such as Abcam, R&D system, Biolegend, and Sigma etc.; further, anti-EpCAM antibody can be selected from the following: Sigma, product number SAB4700423-100UG; R&D system company, product number BAF960; Biolegend, Cat. No. 324216.

The specific recognition molecule is linked to the cell capture carrier via an organic conjugate. The specific recognition molecule can be directly or indirectly linked to the organic conjugate. For example, when the specific recognition molecule is an antibody, the organic conjugate can be linked to streptavidin and then linked to the biotinylated antibody. Specific recognition molecule, such as protein, is usually covalently linked (i.e., directly linked) to a functional group in the conjugate through free amino acid side chain in the structure, for example groups such as sulfhydryl and amino groups. These free amino acid side chain can be naturally occurring or artificially engineered. Those skilled in the art know the specific connection mode of the organic conjugate and the specific recognition molecule. By biotinylating, the specific recognition molecule can also be linked with the organic conjugate that covalently linked with streptavidin to form a recognition molecule-biotin-streptavidin-organic conjugate linking system. The specific connection manner of the connection system is also known to those skilled in the art. Biotinylated specific recognition molecule can be prepared by methods known in the art before use, or commercially available products can be directly used.

The fetal cell circulates in the maternal blood of the pregnant mammal or of the pregnant woman and has a complete fetal genome. The fetal cell in the invention includes nucleated red blood cell (fnrbc) and trophoblast cell (TB). Although the term "cell" is used in the application, it should be understood that the cell includes fragments and/or fragments of cells that carry ligands that specifically recognize the surface of the molecule. The liquid containing fetal cell(s) in the invention includes buffer solutions, culture solutions, peripheral whole blood, cervical swab dispersion or suspension of a pregnant mammal or a pregnant woman, etc., and also includes non-pregnant peripheral blood or cervical swab dispersion/suspension containing fetal cell(s), wherein the fetal cell(s) is/are artificially added to the non-pregnant peripheral blood or cervical swab dispersion/suspension.

The organic conjugate containing one or more disulfide bonds refers to an organic small molecule fragment containing at least one disulfide bond.

In the formula of -A-X— in the invention, when X is —S—$(B)_p$-D- and B is

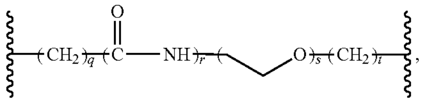

p=0-10, for example, 0, 1, 2, 3, 4, 5, 6, 7, 8, 9; q, r, t is 0-10, respectively, for example 0, 1, 2, 3, 4, 5, 6, 7, 8, 9, 10; preferably 1-5; s is 0-115, for example 10, 20, 30, 40, 50, 60, 70, 80, 90, 100, preferably 20-50.

When A is

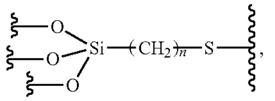

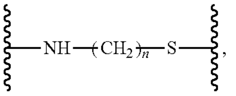

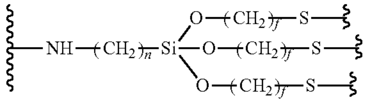

or

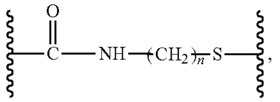

n=1-10, f=1-19, for example, n, f can be 1, 2, 3, 4, 5, 6, 7, 8, 9, 10, respectively, preferably n=3-8, f=2-8.

When X is selected from

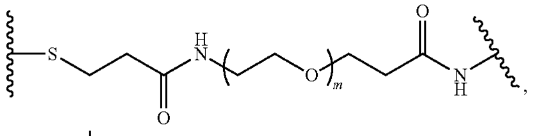

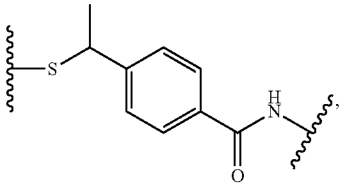

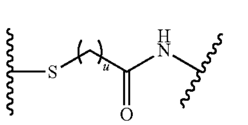

or

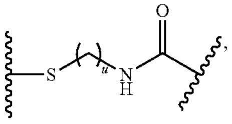

m=0-115, for example, 10, 20, 30, 40, 50, 60, 70, 80, 90, 100, preferably 20-50; u=1-10, for example 1, 2, 3, 4, 5, 6, 7, 8, 9, 10, preferably 2-8.

The organic conjugate comprising one or more disulfide bonds of the invention can be directly or indirectly immobilized on the surface of the cell capture carrier through weak intermolecular interactions (e.g., hydrogen bonds, hydrophobic interactions, etc.) and/or covalent interactions. When the organic conjugate is attached to the surface of the cell capture carrier, the whole organic conjugate can be fixed on the surface of the carrier, or a part of the organic conjugate can be fixed on the surface of the carrier first, and then other parts of the organic conjugate can be reacted with the surface of the carrier, and finally, all the organic conjugates are immobilized on the surface of the carrier. The organic conjugate or part of the organic conjugate can be linked to the specific recognition molecule as described above before being immobilized on the surface of the carrier; or can be linked to the specific recognition molecule after being immobilized on the surface of the carrier. It should be understood that the organic conjugate or part of the organic conjugate comprising one or more disulfide bonds, before being connected to the capture carrier and/or the specific recognition molecule, and/or the part of the organic conjugate, before being connected to each other, may contain reactive groups for attachment to the capture carrier, the specific recognition molecule or another part of the organic conjugate. These groups will be removed due to the reaction after the connection is completed to form a new chemical bond.

For example, the cell capture carrier can be first sulfhydrylated, i.e., a partial fragment of an organic conjugate containing one or more disulfide bonds can be immobilized on the surface of the carrier. The reagent used for sulfhydrylated in the invention can be selected according to the material of the carrier. When the carrier material is polydimethylsiloxane (PDMS), glass, polymethyl methacrylate (PMMA), the sulfhydrylated reagents for the carrier surface include mercaptosilane derivatives (such as (3-mercaptopropyl)trimethoxysilane (MPTS), mercaptoethyl-trimethoxysilane, (4-mercaptobutyl)trimethoxysilane (MPTS)), etc. When the carrier material is polycarbonate, the sulfhydrylated reagents for the carrier surface include mercaptoamino compounds (such as 3-mercapto-2-propylamine, 5-amino-1-mercapto-pentane), aminosilylation reagents (such as 3-aminopropyltriethoxysilane). Part of the organic coupling body used for connecting with the sulfhydrylated carrier can be a linear or branched polyethylene glycol derivative, one end of which is a thiol group, for coupling with the sulfhydrylated carrier. In some instances, before being linked to the specific recognition molecule, the polyethylene glycol derivative contains one or more functional groups, such as maleimide, N-hydroxysuccinimide ester, alkynyl derivatives, azido derivatives, etc., that can be directly or indirectly linked to the specific recognition molecule. A preferred partial organic conjugate attached to the sulfhydrylated carrier may be aromatic disulfide polyethylene glycol succinimidyl valerate, examples of which include, but are not limited to, o-pyridyl disulfide polyethylene glycol succinimidyl valerate (OPSS-PEG-SVA), m-pyridyl disulfide polyethylene glycol succinimidyl valerate, p-pyridyl disulfide polyethylene glycol succinimidyl valerate.

Exemplarily, in the invention, the microfluidic chip can be modified with one or more recognition molecules (such as the preferred anti-EpCAM antibody and anti-CD71 antibody of the invention) using the following scheme: (3-mercaptopropyl)trimethylmethane (MPTS) in a solvent is introduced into the microchip, repeatedly at intervals for a period of time. The solvent is preferably ethanol, and the above operation can be performed by using a manual syringe or an automatic micro-injector, wherein the automatic injector can preferably be a Harvard Apparatus Pump 11 Pico Plus Elite syringe pump, US. The channel is then rinsed several times with solvent and heated in an oven, optionally at a temperature of 60 to 100° C., more preferably 100° C., for the most efficient surface sulfhydrylation. The chip is taken out, cooled to room temperature, and a solution of aromatic disulfide polyethylene glycol succinimidyl valerate in a solvent (e.g., ethanol) is introduced. The concentration of the solution can be 0.005% to 10% (mass fraction), preferably 0.01% (mass fraction). The aromatic disulfide polyethylene glycol succinimide valerate is preferably o-pyridyl disulfide polyethylene glycol succinimide valerate or m-pyridyl disulfide polyethylene glycol succinimide valerate.

After a period of reaction, the chip is rinsed with deionized water, and then rinsed several times with the rinse solution, and then the recognition molecule(s), such as antibody/antibodies, amino-modified nucleic acid aptamer (s), etc., is/are introduced into the microchannel. The concentration of the recognition molecule can be 5 μg/ml to 1000 μg/ml, more preferably 20 μg/ml. After incubating for several hours, the chip interface modified with recognition molecule(s) is obtained. The chip is placed in a refrigerator, such as a 4° C. refrigerator, for later use. The modification results of the recognition molecule can be verified by fluorophore, for example by secondary antibodies with fluorescence or complementary chains of nucleic acid aptamers with fluorescence. Imaging was performed using an inverted fluorescence microscope (brands can be Nikon, Zeiss, Leica and other inverted fluorescence microscopes). When the ratio of the fluorescence value of the positive chip to the fluorescence value of the negative chip is greater than or equal to 1.5, it proves that the recognition molecule modification is successful.

In the invention, the recognition molecule of the microfluidic chip (such as the preferred anti-EpCAM antibodies and anti-CD71 antibodies of the invention) can also be modified using the following scheme: The recognition molecule(s) is/are linked to the microfluidic chip through biotin-streptavidin interaction, with the organic conjugate being modified as described above. After the organic conjugate(s) is/are modified to the microchip, the chip is washed with deionized water and buffer, and then 5 μg/ml to 1000 μg/ml, preferably 15 μg/ml streptavidin is introduced into the microchannel and incubated to obtain the microfluidic chip interface containing streptavidin, and the chip is placed in a 4° C. refrigerator for later use. One hour before use, after taking out the chip, rinse it several times with buffer, and then biotinylated recognition molecule(s) with a concentration of 5 μg/ml to 1000 μg/ml, preferably 20 μg/ml, is/are introduced into the microchannel to obtain microchannel modified with recognition molecule(s).

In the invention, the one or more disulfide bonds in the organic conjugate are chemically cleaved by cell release solution, to release the cells. The preferred cell release solution may preferably be dithiothreitol solution, tris(2-carboxyethyl) phosphine solution, glutathione solution, etc., and the concentration may preferably be 10 mM to 100 mM, such as 10 mM, 20 mM, 30 mM, 40 mM, 50 mM, 60 mM, 70 mM, 80 mM, 90 mM, 100 mM, more preferably 50 mM dithiothreitol solution. An exemplary specific process is to introduce the cell release solution through the capture module or microfluidic chip that has captured cells, then to incubate and rinse the chip, and collecting the released cell suspension.

In the present invention, the peripheral blood of a pregnant women is usually the peripheral blood collected from pregnant women from 7 weeks of gestation to before delivery. It should be understood that in order to prevent coagulation in the art, the collected peripheral blood of pregnant women will be stored in special blood collection tubes, and these blood collection tubes usually contain anticoagulants (e.g. dipotassium EDTA), buffers or other additives. When using the capture module or the microfluidic chip for capturing fetal cell(s) of the invention to capture and isolation the peripheral blood of pregnant women, or other liquids containing fetal cell(s), nuclear dye, fluorescent tracer, and the like can also be added to assist in cell tracking.

Beneficial Effects of the Present Invention

The capture module and microfluidic chip of the present invention can capture fetal cell(s) from whole blood without pre-treatment for initial isolation, overcoming the cell defects caused by the needed pre-isolation in the prior art and improving the final capture and release efficiency.

The use of the capture module and the microfluidic chip of the present invention to capture fetal cell(s) enables high capture efficiency and purity, and background interference can be effectively avoided, making it possible to capture a very small amount of fetal cells in the liquid.

The use of the capture module and the microfluidic chip of the present invention to capture fetal cell(s) enables the efficient and accurate non-invasive release of captured fetal cell(s), improves the purity of recovered fetal cell(s), and avoids background contamination caused by direct injection of cell lysate or enzymatic solution into the chip which prevents whole genome analysis; it also avoids the complex operation of using laser cutting or capillary microscopic picking and the inability to obtain cells in batch. In addition, the capture module and microfluidic chip of the present invention capture fetal cell(s) while achieving controlled release of the small number of fetal cells. The above advantages are important for removing contaminants as much as possible and for performing downstream analysis efficiently.

BRIEF DESCRIPTION OF THE DRAWINGS

FIGS. 1A and 1B are the schematic diagram and the photograph of the overall structure of the microfluidic chip.

FIG. 2 is the schematic diagram of the arrangement and parameters of the microcolumns in the microfluidic chip microarray (not the actual scale). The horizontal distance between the orthocenter of adjacent microcolumns in the same row is x. The offset distance of the orthocenter of the latter microcolumn relative to the orthocenter of the previous microcolumn along the vertical direction of the fluid microchannel plane is Δy. The distance from the bottom of the previous microcolumn to the top of the next microcolumn in the same column along the vertical direction of the fluid microchannel plane is y.

FIG. 5A is the whole genome copy number analysis of the captured fetal cells; FIG. 5B is the whole genome copy number analysis of the original cell solution.

EMBODIMENTS

Figure 3A:
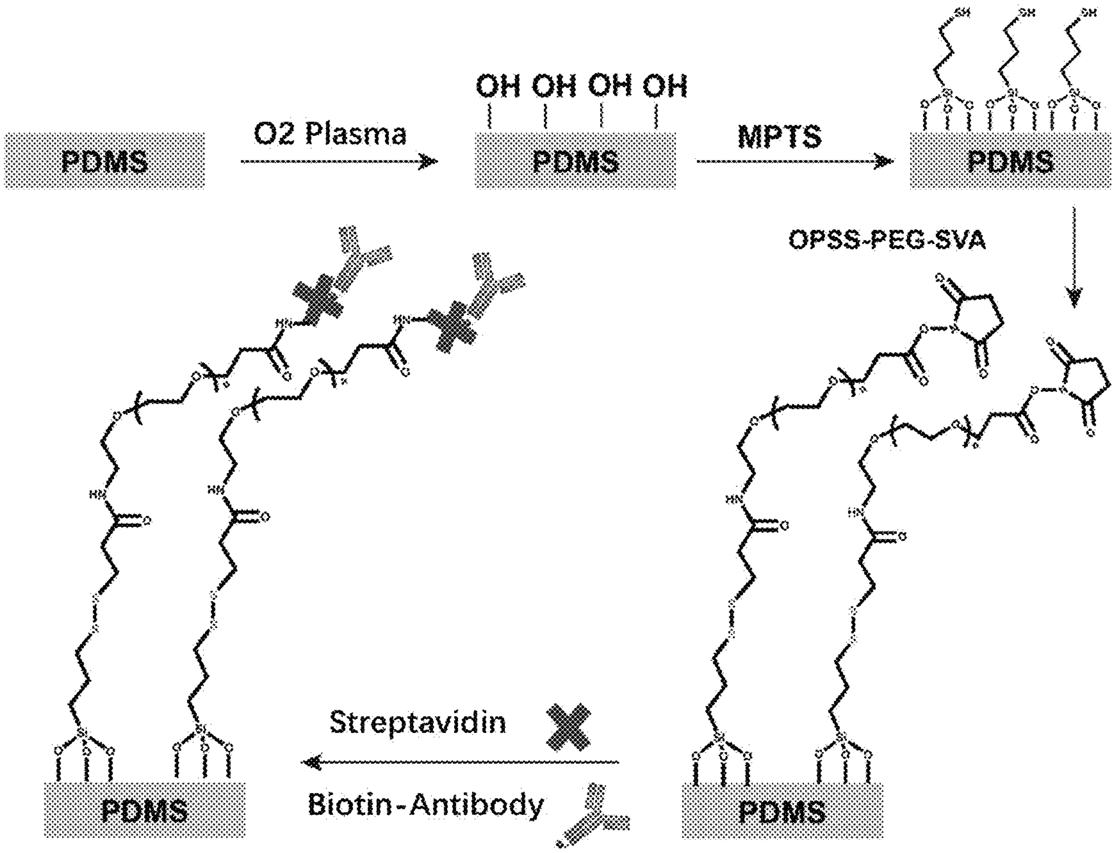
FIG. 3A is the schematic flow diagram of modifying specific recognition molecules to a microfluidic chip.

Example 1 Experimental Example of Magnetic Beads+Antibodies Modified by Disulfide Bonds

1.1 Experimental Method

The magnetic beads were Dynabeads™ MyOne™ Carboxylic Acid obtained from Thermo Fisher with item number of 65012, and the method of using the magnetic beads is described in the instructions for use, which is shown as follows: The beads were removed, shaken and mixed, 20 L of the beads were washed three times with 15 mM MES buffer pH 6.0, a solution of 1-(3-dimethylaminopropyl)-3-ethylcarbodiimide hydrochloride was added (see instruction for concentration), allowed to react for 30 min and magnetically separated, then washed 3 times with 15 mM MES buffer pH 6.0. 3-sulfhydryl-2-propanamine was added, allowed to react for 30 min, magnetically separated and washed 3 times with 15 mM MES buffer pH 6.0. A solution of 0.01% (mass fraction) of m-pyridyl disulfide polyethylene glycol succinimidyl valerate (with the polyethylene glycol molecular weight of 2000) was added, allowed to react for 30 min, magnetically separated, and washed e times with 15 mM MES buffer pH 6.0. 20 μg/mL of recognition antibodies were added, incubated for 1 h at room temperature, washed 3 times with 1×PBS+0.01% BSA, and immunomagnetic beads (resuspended in 20 μL of buffer) were obtained. 5 μL of immunomagnetic beads were mixed with 2 mL of peripheral blood of pregnant women, incubated for 45 min at room temperature, and magnetically separated. The cells obtained by magnetic separation were stained with antibodies and analyzed by fluorescence microscopy imaging. In which, the blood processing method is referred to step 3.1 in Example 3 below. After achieving cell capture, a solution of 100 μL of 50 mM DTT was introduced, allowed to react at 37° C. for 10 minutes, magnetically separated. The number of cells in the supernatant was counted, and cell activity was analyzed, referring to Example 4 4.1 for the specific steps, and the results are shown in Table 1.

2) Comparative Example 1

Experiments were performed with reference to the same methods as described above, with the difference that after cell capture, 100 μl of commercial trypsin (Thermo Fisher, Trypsin-EDTA (0.25%), phenol red, item number 25200056) was taken for cell release. The analysis of the viability of the released cells was performed referring to the method of Example 4 4.1.

1.2 Experimental Results

TABLE 1

Comparison of disulfide bond chemical cleavage release and trypsin release methods with magnetic beads as cell capture carriers

| Example | Release Efficiency | Recovery Efficiency | Purity prior to Release | Purity after Release | Cell Viability |
|---|---|---|---|---|---|
| Example 1.1 | 85.30% ± 6.03 | 64.50% ± 6.18 | 2.22% ± 1.12 | 56.47% ± 9.36 | 85.60% ± 2.90 |
| Comparative Example 1 | 69.75% ± 0.16 | 40.56% ± 5.90 | 1.23% ± 0.04 | 15.23% ± 1.05 | 53.6% ± 2.10 |

Example 2 Preparation of Microfluidic Chip for Fetal Cell Capture

The microfluidic chip was fabricated with reference to the structure shown in FIGS. 1A and 1B. The mask version of the chip is a silicon-based chip containing su-8 photoresist channels obtained by UV lithography. The dimethylsiloxane (PDMS) prepolymer was poured into the chip, and the PDMS channel layer containing microfluidic channels can be obtained after a four-step operation of pumping, heating, demoulding, and punching. The PDMS channel layer and the slide are bonded to the complete chip using a plasma cleaner (Harrick, model: PDC-002). The preferred slide was a 25.4×76.2 mm non-frosted edge slide (brand Sailboat).

The chip is set with two inlets: inlet (1) and inlet (2), and one outlet: outlet (3), and a fluidic microchannel set with microarrays between the inlet and outlet, the structure of which is shown in FIGS. 1A and 1B. In this example, the inlets and outlet were prepared using a microfluidic chip punch pen, and the size of the punch pen is preferably (ID*OD, mm) 3.3×4.0, 3.3×3.5, 2.4×3.0, 2.3×2.8, 1.9×2.4, 1.6×2.1, 1.2×1.8, 0.9×1.3, 0.6×0.9, 0.5×0.8, 0.4×0.7, more preferably, the inlet size is 0.4×0.7 and the outlet size is 1.2×1.8.

As a specific example (see FIG. 2), the microfluidic chip used for cell capture and release in the following example is 4 cm long and 1 cm wide, and the inlet (1) is a blood sample inlet and (2) is a buffer inlet with the use of the same flow rate for simultaneous injection. The fluidic microchannel between the inlet and the outlet is set with trigonal microcolumns arranged in rows. The microcolumns have a triangular cross-sectional side length of 80 m, a rotation angle of 15°, a column height of 50 m, an x value of 122 m, ay value of 32 m, and a Δy value of 3.5 m.

The coupling of recognition molecules can be performed by two methods, respectively, as follows:

Recognition molecule coupling method I: directly coupling the recognition molecule to the microchannel, as follows: the fluid microchannel of this specific example was irradiated by a plasma cleaner and immediately adhered to the carrier slide, and 20 μL ethanol solution of (3-mercaptopropyl)trimethoxysilane (MPTS) with a volume ratio of 4% was introduced every 5 minutes for 1 h. The operation can be performed by manual syringe injection or by automatic injection using an automatic microsampler, preferably Harvard Apparatus Pump 11 Pico Plus Elite syringe pump, US. Immediately afterwards, the channels were washed 3 times with ethanol solution, 100 μl each time, and placed in an oven for one hour at a heating temperature of 100° C. to obtain the highest efficiency of surface sulfhydrylation. The chip was taken out, cooled to room temperature and 0.01% (mass fraction) of o-pyridyl disulfide polyethylene glycol succinimidyl valerate (with the polyethylene glycol molecular weight of 2000) was introduced.

After 30 minutes of reaction, the microchannels were rinsed with deionized water and 3 times with PBS buffer, 100 μl each time, and then 20 μg/ml of recognition molecules containing amino groups were introduced into the microchannels and incubated for 1 hour to obtain a fluid microchannel interface containing recognition molecules, and the chip was placed in a refrigerator at 4° C. for use. After chip preparation, the chip was washed 3 times with PBS buffer, 100 μl each time, and secondary antibodies containing 20 μg/ml with fluorescence or 10 μM complementary strand of nucleic acid aptamers with fluorescence were introduced, incubated for 30 minutes, and then the chip was washed 3 times with PBS buffer, 100 μl each time, and imaged using an inverted fluorescence microscope (Nikon inverted fluorescence microscope), and when the ratio of the fluorescence value of the modified positive chip to that of the unmodified negative chip was greater than or equal to 1.5, the successful modification of the recognition molecule was demonstrated.

Recognition molecule coupling method II: The recognition molecules were attached to the microchannels by biotin-streptavidin interaction as follows: the microchannels of this specific example was immediately adhered to the carrier slide after irradiation through a plasma cleaner, and 20 μL ethanol solution of (3-mercaptopropyl)trimethoxysilane (MPTS) with a volume ratio of 4% was introduced every 5 minutes for 1 h. The operation can be performed by manual syringe injection or by automatic injection using an automatic microsampler, preferably Harvard Apparatus Pump 11 Pico Plus Elite syringe pump, US. Immediately afterwards, the channels were washed 3 times with ethanol solution, 100 μl each time, and placed in an oven for one hour at a heating temperature of 100° C. The chip was taken out, cooled to room temperature and 0.01% (mass fraction) of aromatic disulfide polyethylene glycol succinimidyl valerate, preferably o-Pyridyl disulfide polyethylene glycol succinimide valerate (with the polyethylene glycol molecular weight of 2000) was introduced.

After 30 minutes of reaction, the microchannels were rinsed with deionized water and 3 times with PBS buffer, 100 μl each time, and then 15 μg/ml of streptavidin were introduced into the microchannels and incubated for 1 hour to obtain a fluid microchannel interface modified with streptavidin, and the chip was placed in a refrigerator at 4° C. for use. One hour before use, the chip was taken out and rinsed 3 times with PBS buffer, 100 μl each time, then 20 μg/ml of recognition molecule containing biotin (human EpCAM/TROP1 biotinylated purified PAb, item number BAF960) was introduced into the microchannels and incubated for 1 hour to obtain a fluidic microchannel containing the recognition molecules. A schematic diagram of the coupling steps can be seen in FIG. 3A.

In the following, the effect of capture/release of fetal cells were tested using the chip made by Coupling Method II.

Example 3 Testing of the Capture Efficiency of Microfluidic Chip on Fetal Cells

3.1 Experimental Method

The microfluidic chip obtained by the recognition molecular coupling method II in Example 2 was taken and the chip was blocked for 30 minutes using 3% bovine serum albumin solution as the blocking solution.

An additional culturable cell line was added to 1 mL of healthy human peripheral blood to simulate the peripheral blood environment of a pregnant woman (the culturable fetal cell line was JEG-3 (human choriocarcinoma cell line), purchased from the Cell Resource Center, Shanghai Institutes for Biological Sciences, Chinese Academy of Sciences, catalog number TCHu195). Specifically, the blood contained approximately 100 JEG-3 cells, $9.63\times10^6$ leukocytes per mL and $3.98\times10^9$ erythrocytes per mL. The obtained blood was introduced by a syringe pump through the inlet (1), while the inlet (2) was simultaneously fed with buffer, at a flow rate of 0.3 mL/h. After the blood was completely introduced, the chip was rinsed with PBS buffer at a flow rate of 1.0 mL/h for 15 minutes. The JEG-3 cell line was pre-stained with calcein before being added to the blood to differentiate target cells from blood cells.

Figure 3B:
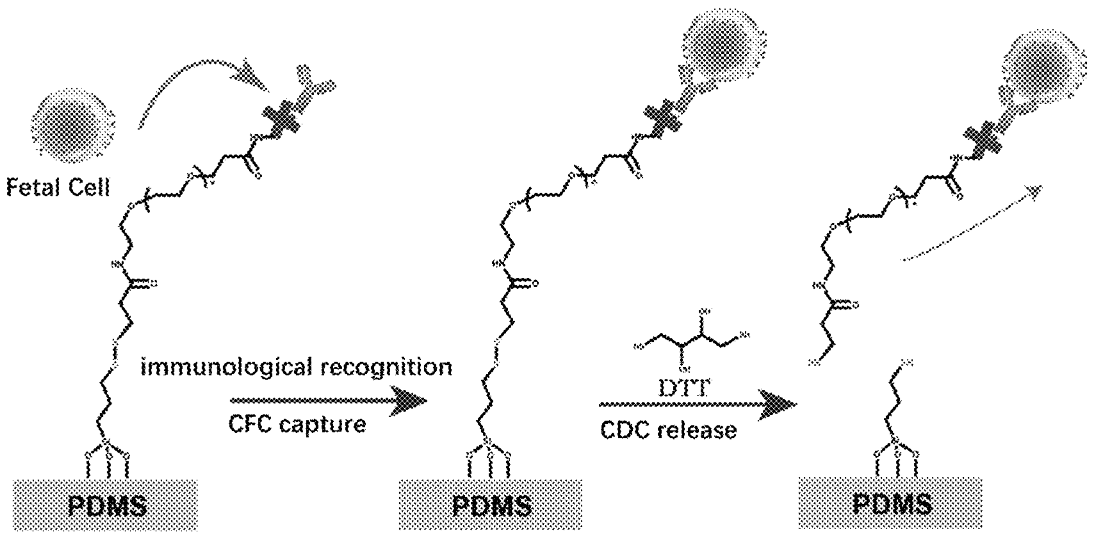
FIG. 3B is the schematic diagram of the process of capturing and releasing fetal cells by the modified microfluidic chip.

The staining method was: the cells were digested for 10 minutes using 0.02% EDTA (disodium EDTA) digestion solution at pH between 7.2 and 7.4, then the digestion solution was removed, and PBS buffer was added, and the cells were blown down to obtain a concentration of $1*10^5$ cells/ml. 200 μl of cell solution was added 1 μl of calcein solution (Thermo Fisher, item number C34852), stained at 37° C. for 10 minutes, and washed 3 times with 500 μl of PBS buffer and centrifuged at 1000 g for 3 minutes each time to obtain pre-stained cell solution. A schematic diagram of the capture steps can be seen in FIG. 3B.

The chips were washed and imaged by inverted fluorescence microscopy (excitation by blue laser). The number of fluorescent cells was counted to examine the capture efficiency of fetal cells, and the results are shown in Table 2.

Wherein, human B lymphocytoma cells Ramos and leukocyte WBCs were used as negative cells to examine the effect of specific recognition as well as non-specific adsorption of the chip. The operation was performed with reference to the treatment for JEG-3 cells.

3.2 Experimental Results

TABLE 2

Analysis of capture efficiency

| Cell Type | Simulated Fetal Cells | Human B Lymphocytoma Cells Ramos | Leukocytes |
|---|---|---|---|
| Capture Efficiency | 92.3 ± 1.2% | 3.2 ± 2.0% | 0.08 ± 0.006% |

3.3 Comparative Example 2

Effect of Blood Pretreatment on Cells Capture

100 JEG-3 cells were added to 1 mL of human peripheral whole blood to simulate the peripheral blood of pregnant women. The treatment of JEG-3 was performed with reference to the experimental method described in 2.1. 3 different methods were used for comparative analysis: 1) the whole blood was directly introduced into the chip for injection analysis without any treatment; 2) the peripheral blood and the prepared gradient separation solution (percoll density used 1.090) in a 4:3 volume ratio were taken into a centrifuge tube and centrifuged at 400 g for 30 min at 18-20° C. After centrifugation, four layers of solution were obtained, which are mature erythrocytes, centrifugal liquid layer, monocyte layer, platelets and plasma layer, and the monocyte layer was removed with a pasteur pipette, transferred to a 2 mL centrifuge tube, centrifuged, washed, and finally resuspended in 300 μL PBS for later use; 3) a erythrocyte lysate (potassium bicarbonate ($KHCO_3$) 1.0 g; ammonia chloride ($NH_4Cl$) 8.3 g; EDTA-$Na_2$ 0.037 g, double distilled water was added to 1000 mL, the erythrocyte lysis solution was then obtained) was taken, 5 volumes of which were mixed upside down with blood for 5 minutes, and the lysed solution was centrifuged at 400-500 g for 5 min, the red supernatant was discarded, and centrifuged at 4° C. for better effect to enrich the bottom mononuclear cells, and resuspended in 300 μL PBS for later use.

The samples treated by the above three methods were introduced into the microfluidic chip using the same method as in 3.1, with a flow rate of 0.3 mL/h, respectively. After washing, the chip was imaged by inverted fluorescence microscopy (excitation by blue laser), and the number of fluorescent cells was counted to examine the capture efficiency of fetal cells. The cell counts before and after capture by microfluidic chip under different peripheral blood treatment methods are shown in Table 3 and Table 4, respectively.

TABLE 3

Cell counts before capture by chip under different peripheral blood treatment methods

| Example | Method of Treating Peripheral Blood | Leukocytes/ mL | Erythrocytes/ mL | Target cells |
|---|---|---|---|---|
| Example 3.1 | Untreated Blood | $9.63 \times 10^6$ | $3.98 \times 10^9$ | 200 ± 3 |
| Comparative | Percoll 1.090 | $7.03 \times 10^6$ | $0.05 \times 10^9$ | 120 ± 20 |
| Example 2 | Lysis of Erythrocytes | $2.61 \times 10^6$ | $0.07 \times 10^9$ | 70 ± 25 |

Although pre-treatment of blood can remove some red blood cells and serum, and reduce the complexity of the cell sample, it also causes variable cell loss.

In contrast, the technical solution of the present application allows for the running of whole blood. Thus, the loss of cells can be further reduced with few cells to be captured.

TABLE 4

Cell counts after capture by chip under different peripheral blood treatment methods

| Example | Method of Treating Peripheral Blood | Leukocytes | Target Cells |
|---|---|---|---|
| Example 3.1 | Untreated Blood | ~2000 | ~180 |
| | Percoll 1.090 | ~1500 | ~108 |
| Comparative Example 2 | Lysis of Erythrocytes | ~1000 | ~63 |

Note:
Since erythrocytes do not contain nuclei and will not affect subsequent analysis, they are not included in the statistical analysis.

Example 4 Assaying of the Release Efficiency of Fetal Cells 4.1 Experimental Method 1) The fetal cells captured in Example 3 were released using the chemical cleavage method, the specific process are as follows: a solution of 50 mM dithiothreitol was introduced into the chip that had captured cells (inlet 1), which was incubated at 37° C. for 10 min, and then rinsed using PBS buffer containing 3% bovine serum albumin at a flow rate of 3 mL/h, with a total volume used of 1 mL, and the released cell suspension was collected through the outlet (3).

2) The release efficiency was calculated by comparing the number of cells in the chip before and after release. The recovery rate of cells after release was counted by counting the number of cells in the final 1 ml of cell suspension. The reason for the difference between the release efficiency and the recovery rate may originate from the adsorption of cells by the channel during the collection process. This can be somewhat improved by blocking the chip with a blocking solution, which is a 3% bovine serum albumin solution. The number of cells was counted according to 3.1 Experimental Methods. A schematic diagram of the release steps can be seen in FIG. 3B.

(3) Viability analysis of the cells after release: the conventional double staining method (i.e. Calcein-AM (Calcein-AM) and propidium iodide (PI) solution) was used to analyze the viability of released cells. The specific method is described as follows: the recovered suspension of post-release cells was taken and centrifuged at centrifugal concentration, 1000 g for 3 min, to obtain 200 μl of suspension. 1 μl of Calcein-AM (Thermo Fisher, No. C3099) and 1 μl of PI solution (Sigma, No. P4864) were added and incubated for 30 min at 37° C. Imaging analysis was performed using a fluorescent inverted microscope. The number of live cells was obtained using filter Ex 465-495 nm/BA 521-558 nm imaging, and the number of cells was obtained using filter Ex 520-555 nm/BA 570-630 nm imaging. Cell viability was calculated as Cell viability=number of live cells/(number of live cells+number of dead cells)*100.

(4) Comparative Example 3

Trypsin digestion was used to release the fetal cells captured in Example 3 by introducing a 0.25% trypsin solution (Thermo Fisher, item number 25200056) into the chip that had captured cells (inlet 1), which was then incubating for 3 minutes at 37° C., and rinsing using PBS buffer containing 3% bovine serum albumin at a flow rate of 3 mL/h, with a total volume of 1 mL. The released cell suspension was collected through the outlet (3). Subsequent cell viability analysis experiments were performed with reference to experiment 4.1 (3).

4.2 Experimental Results

Figure 4:
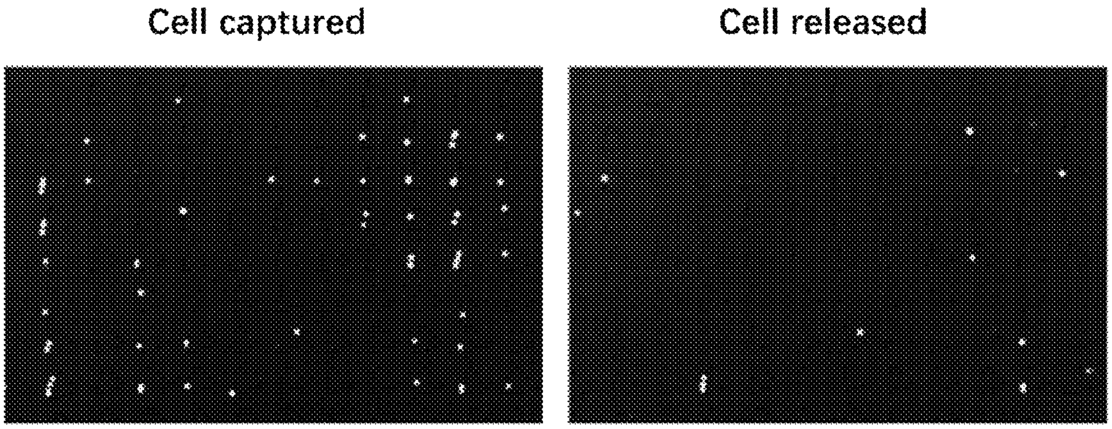
FIG. 4 is a fluorescent cell imaging before and after release of the fetal cells that has been captured by the microfluidic chip, and the white light spots are the captured cells.

The visual graphical reference of the release is shown in FIG. 4. The cells captured to the same position can be specifically released by the action of the cell release solution, and the statistical results are shown in Table 5.

TABLE 5

Analysis of cell release efficiency, recovery rate and post-release viability

| Example | Release Efficiency | Recovery Efficiency | Purity prior to Release | Purity after Release | Cell Viability |
|---|---|---|---|---|---|
| Example 4.1 | 93.47% ± 6.99 | 73.34% ± 3.49 | 52.23% ± 4.84 | 86.46% ± 3.86 | 92.75% ± 0.16 |
| Comparative Example 3 | 79.75% ± 4.16 | 50.56% ± 5.23 | 50.43% ± 4.04 | 55.23% ± 5.45 | 63.6% ± 4.34 |

Example 5 Genome and Transcriptome Analysis of Captured Cells

5.1 Experimental Method

1) Genomic analysis: Fetal cells released from Example 4 were collected in a 1.5 ml RNase-free Eppendorf tube and the supernatant was removed by centrifugation (1000 g for 3 min). The volume was concentrated to 10 μl and DNA was recovered using a DNA extraction kit or by thermal lysis. Thermal lysis was used for lysis in this example. Comparative experiments showed that the lowest DNA loss rate was obtained with the thermal lysis treatment. Samples were placed on a 95° C. heater, thermally lysed for 10 minutes, and then placed in a −80° C. refrigerator for storage (note: samples were stored for no more than 48 hours). DNA samples were tested using Bio-Rad's PrimePCR ddPCR assay kit, which detects the EGFR L858 mutation (Item #1863104; EGFR L858 mutation was detected here because the mutation occurred in the cells that were admixed, whereas normal blood samples were wild-type, as a way to perform specific analysis of the genetic analysis of the enriched cells). Data were analyzed using the Bio-Rad companion package to calculate the number of EGFR L858 mutations detected from a single sample.

2) Transcriptome analysis: Fetal cells released from Example 4 were collected in a 1.5 ml RNase-free Eppendorf tube, the supernatant was removed by centrifugation (1000 g for 3 min). The volume was concentrated to 10 μl, and RNA recovery was performed with an RNA extraction kit. In this example, Zymo Research Corp's TRI Reagent (Item No. R2050-1-50) was used for cell lysis, and the experimental method was referred to the instructions. The collected RNA was purified using Zymo Research Corp's Direct-zol RNA MicroPrep (Item No. R2060) kit, and the experimental method was referred to the instructions. After obtaining the RNA, reverse transcription kits were used to reverse transcribe the RNA into cDNA. cDNA was reverse transcribed from the purified RNA using the Scientific Maxima H Minus (Item M1661) Reverse Transcriptase Kit from Thermo Fisher. The cDNA samples were tested using Bio-Rad's PrimePCR ddPCR assay kit, which covered 14 ROS1 gene rearrangement isoforms (item number qHsaCID0016464; the ROS1 gene was tested here because of the high expression of the adulterated cells and the absence or low expression of the normal blood). Data were analyzed using the Bio-Rad companion software package to calculate the corresponding copy number of ROS1 rearrangements detected from individual samples.

3) Comparative Example 4, the method of lysis in the chip is briefly described: the microfluidic chip that had captured cells obtained in Example 3 was recovered for DNA or RNA. The recovery method was performed using the recovery kits described in steps 1) and 2) of Example 5.1 above. The corresponding reagents were introduced directly into the chip for cell lysis, and then the solution was aspirated and further purified.

5.2 Experimental Results

1) For the detection of gene mutations in rare cells, the release method of the invention is superior to the method of direct cell lysis on a chip. The method of the invention can maintain a higher gene concentration, which in turn improves the detection rate and reduces the false negative rate. As shown in Table 5 below, even if the number of cells was as low as 2, the chip of the application can still obtain a better detection rate. In contrast, the detection rate was very low even when the number of cells was as high as 25 in Comparative Example 4.

TABLE 6

Detection rate ratio analysis for mutant/wild type

| Example | 2 cells captured | 13 cells captured | 25 cells captured |
|---|---|---|---|
| Example 5.1 | 46.87% ± 1.96 | 49.43% ± 2.55 | 65.43% ± 3.96 |
| Comparative Example 4 | 1.61% ± 0.17 | 1.60% ± 0.10 | 12.37% ± 0.80 |

2) The results of detection of the cellular transcriptome are shown in Table 7. The release method of the invention is superior to the method of cell lysis directly on the chip, maintaining a higher gene expression analysis, which in turn improves the detection rate and reduces the false negative rate.

TABLE 7

| Copy number analysis for transcriptome ROS1 | |
|---|---|
| Example | ROS1 Copy number (k) |
| Example 5.1 | 16.37 ± 1.06 |
| Comparative Example 4 | 8.40 ± 0.79 |

Example 6 Whole Genome Analysis for Fetal Cells

6.1 Experimental Method

1) For the fetal cells released in Example 4, picking of fetal cells was achieved by fluorescence microscopy. The obtained cells were collected in a 0.2 ml of RNase-free Eppendorf tube. The transfer reagent used was controlled to 1 μl or less. Follow-up operations were performed using a commercial whole genome amplification kit, MALBAC® Single Cell Whole Genome Amplification Kit (Shanghai Yikon Medical Laboratory Co., Ltd.). After cell amplification, the product was purified using magnetic beads (for example, Nanjing Vazyme Biotechnology Co., Ltd., item No. N412-01). Whole-genome library was established on the obtained genomes (e.g., Nanjing Vazyme Biotechnology Co., Ltd., item No. TD502-01), and the products were purified using magnetic beads (e.g., Nanjing Vazyme Biotechnology Co., Ltd., item No. N412-01). After quantification, the products were sent to the testing company for sequencing analysis (e.g., Beijing Novogene Technology Co., Ltd, second generation whole genome sequencing analysis, NovaSeq technology (Illumina)). The whole genome copy number of fetal cells was obtained by comparison with the reference sequence number h19.

2) Reference Example

In order to verify the genomic integrity of the obtained cells, the original cell solution without any chip treatment and release was used as a reference for sequencing analysis and comparison with the results of Example 6.1 Step 1). The raw cell solution was processed as follows: $10^5$ cells were taken and genes were extracted using the Genome Extraction Kit (Nanjing Vazyme Biotechnology Co., Ltd., item no. DC111-01). Whole-genome library was established on the obtained genomes (Nanjing Vazyme Biotechnology Co., Ltd., No. TD501-01), and the products were purified using magnetic beads (Nanjing Vazyme Biotechnology Co., Ltd., No. N412-01). After quantification, the products were sent to the testing company for sequencing analysis (Beijing Novogene Technology Co., Ltd, second generation whole genome sequencing analysis, NovaSeq technology (Illumina)). The whole genome copy number of the original cell solution was obtained by comparing with the reference sequence number h19.

6.2 Analysis of Experimental Results

Figure 5A:
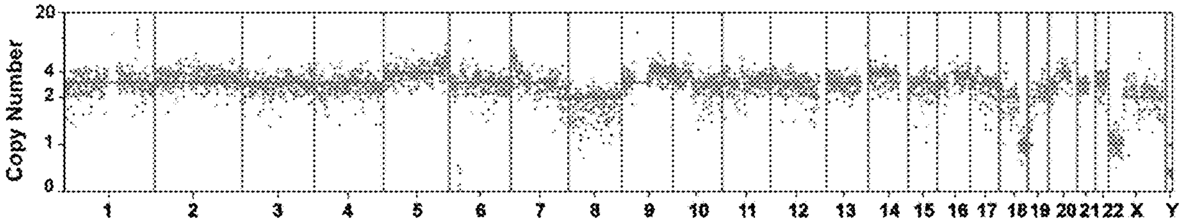
FIGS. 5A and 5B are a calibration comparison diagram of the released fetal cells after amplification and sequencing with the human genome.
Figure 5B:
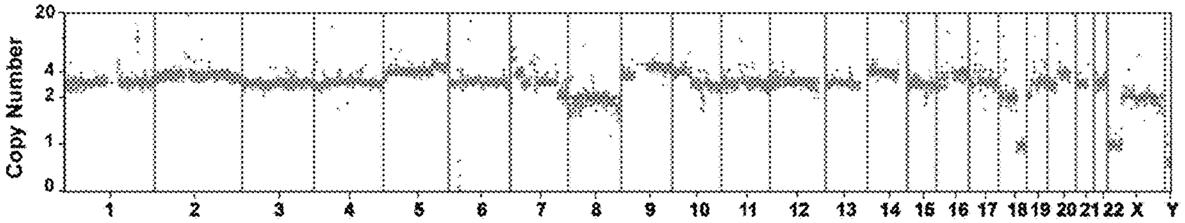

As shown in FIGS. 5A and 5B, the results showed that the cells enriched by the chip (FIG. 5A) still maintained the genetic information of the original parents (FIG. 5B), which provided the premise of fidelity guarantee for the study of fetal genetic diseases, and the method laid the foundation for the screening of genetic diseases.

The invention claimed is:

1. A fetal cell capture module, comprising a cell capture carrier and one or more recognition molecules for specific capture of cell(s), with the one or more recognition molecules being attached to the surface of the cell capture carrier via an organic conjugate L comprising a disulfide bond, wherein the organic conjugate L has the formula:

-A-X—, wherein

A is

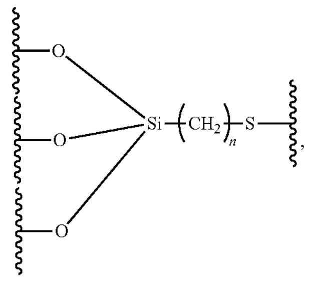

or with A being covalently linked to the capture carrier via the non-sulfur bond end, wherein n=1-10;

X is

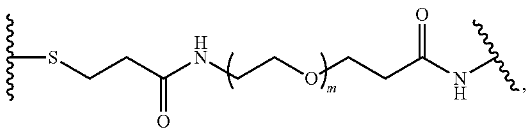

or wherein the sulfur end of X is covalently attached to A to form a disulfide bond, with the other end of X being directly or indirectly connected to the one or more recognition molecules, wherein m=0-115;

wherein the one or more recognition molecules are at least one antibody.

2. The capture module according to claim 1, wherein the organic conjugate L is

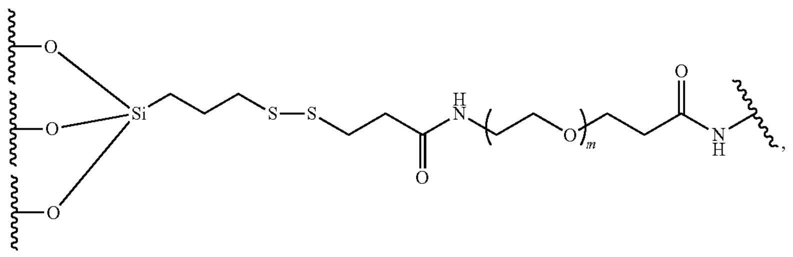

wherein m=0-115.

3. The capture module according to claim 2, wherein m=20-50.

4. The capture module according to claim 1, wherein the one or more recognition molecules are one or both of an anti-EpCAM antibody or an anti-CD71 antibody.

5. The capture module according to claim 1, wherein the fetal cell is a nucleated erythrocyte or a trophoblast cell.

6. The capture module according to claim 1, wherein the cell capture carrier includes a magnetic bead or a microfluidic chip.

7. The capture module according to claim 1, wherein n=3-8; and m=20-50.

8. A method of using the capture module according to claim 1, comprising bringing the capture module in contact with a liquid comprising fetal cell(s) to enable capture of the fetal cell(s);

optionally, the liquid comprising fetal cell(s) comprises peripheral blood, cervical swab dispersion or suspension of a pregnant mammal or pregnant woman, non-pregnant peripheral blood, or buffer or culture solution comprising fetal cell(s);

optionally, the liquid is directly contacted with the capture module without pre-isolation treatment;

optionally, the capture module that has captured the fetal cell(s) is contacted with a chemical cleaving agent to break the disulfide bond of the organic conjugate L to achieve the release of the fetal cell(s), and the chemical cleaving agent is optionally one or more of dithiothreitol, tris(2-carboxyethyl) phosphine, or glutathione.

9. A microfluidic chip for fetal cell capture, wherein the surface of the chip is modified via organic conjugate(s) L comprising a disulfide bond by one or more recognition molecules that specifically capture fetal cell(s), wherein the release of the captured fetal cell(s) is achieved by chemically cleaving the disulfide bond in the organic conjugate L after the fetal cell(s) are captured by the one or more recognition molecules;

wherein the organic conjugate L has the formula:

-A-X—, wherein

A is

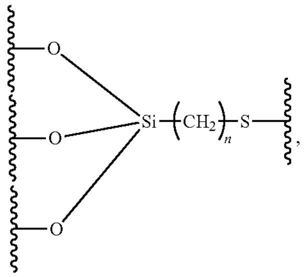

or with A being covalently linked to the chip via the non-sulfur bond end, wherein n=1-10;

X is

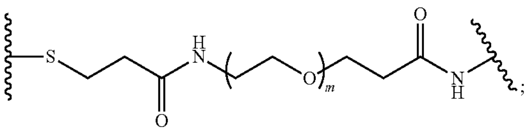

or wherein the sulfur end of X is covalently attached to A to form a disulfide bond, with the other end of X being directly or indirectly connected to the one or more recognition molecules, wherein m=0-115;

wherein the one or more recognition molecules are at least one antibody.

10. The microfluidic chip according to claim 9, wherein the organic conjugate L is

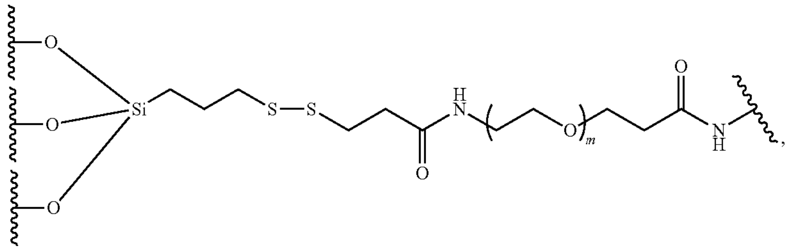

wherein m=0-115.

11. The microfluidic chip according to claim 10, wherein m=2050.

12. The microfluidic chip according to claim 9, wherein the chemical cleaving is achieved by using one or more of dithiothreitol, tris(2-carboxyethyl) phosphine and glutathione.

13. The microfluidic chip according to claim 9, wherein the one or more recognition molecules are one or both of an anti-EpCAM antibody or an anti-CD71 antibody.

14. The microfluidic chip according to claim 9, wherein the fetal cell(s) are a nucleated erythrocyte or a trophoblast cell.

15. The microfluidic chip according to claim 9, wherein the microfluidic chip is provided with one or more inlets, outlets and fluidic microchannels for fluid passage;

the fluidic microchannels are further provided with a microarray comprising a plurality of microcolumns arranged in one or more rows;

the cross-sectional shape of the microcolumns is triangular, and n=3-8; and m=20-50.

16. A method of using the microfluidic chip according to claim 9, comprising:

(1) obtaining a liquid comprising fetal cell(s);

(2) introducing the liquid obtained in step (1) into the microfluidic chip such that the fetal cell(s) in the liquid are brought into contact with the one or more recognition molecules to realize the capture of the fetal cell(s);

optionally, the method further comprising:

(3) introducing a chemical cleavage agent to the microfluidic chip to break the disulfide bond in the organic conjugate L and release the captured fetal cell(s);

optionally, the liquid comprising fetal cell(s) comprises peripheral blood, cervical swab dispersion or suspension of a pregnant mammal or pregnant woman, non-pregnant peripheral blood, non-pregnant cervical swab dispersion or suspension, or buffer or culture solution comprising fetal cell(s);

optionally, introducing the liquid directly into the microfluidic chip without pre-isolation treatment;

optionally, introducing the liquid through the microfluidic chip at a flow rate of 0.1-10 mL/h, or 0.1 to 1 mL/h.

* * * * *